United States Patent [19]

Muth et al.

[11] Patent Number: 5,236,444
[45] Date of Patent: Aug. 17, 1993

[54] ABSORBABLE POLYMERS AND SURGICAL ARTICLES MADE THEREFROM

[75] Inventors: Ross R. Muth, Brookfield; Nagabhushanam Totakura; Cheng-Kung Liu, both of Norwalk, all of Conn.

[73] Assignee: United States Surgical Corporation, Norwalk, Conn.

[21] Appl. No.: 966,948

[22] Filed: Oct. 27, 1992

[51] Int. Cl.$^5$ ................. A61L 17/00; C08G 63/64; C08G 63/08; C08G 63/06
[52] U.S. Cl. .................. 606/230; 525/411; 525/413; 525/415; 528/354
[58] Field of Search ............. 606/230; 525/411, 413, 525/415; 528/354

[56] References Cited

U.S. PATENT DOCUMENTS

| | | | |
|---|---|---|---|
| 3,636,956 | 1/1972 | Schneider | 128/335.5 |
| 4,243,775 | 1/1981 | Rosensaft et al. | 525/415 |
| 4,300,565 | 11/1981 | Rosensaft | 525/415 |
| 4,429,080 | 1/1984 | Casey | 525/415 |
| 4,705,820 | 11/1987 | Wang et al. | 524/381 |
| 4,891,263 | 1/1990 | Kotliar et al. | 428/225 |
| 4,916,193 | 4/1990 | Tang et al. | 525/413 |
| 4,920,203 | 4/1990 | Tang et al. | 525/409 |
| 4,965,300 | 10/1990 | Eichenauer et al. | 525/415 |
| 5,080,665 | 1/1992 | Jarrett et al. | 606/219 |

Primary Examiner—David J. Buttner
Attorney, Agent, or Firm—Thomas R. Bremer; Peter G. Dilworth; Rocco S. Barrese

[57] ABSTRACT

Block copolymers have a first polymer block wherein glycolide is the predominant component and a second block having glycolide, lactide and trimethylene carbonate linkages. The copolymers are useful in forming surgical devices, including monofilament sutures.

20 Claims, 2 Drawing Sheets

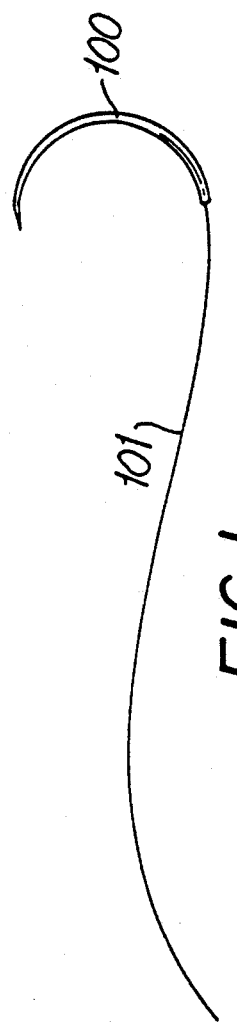
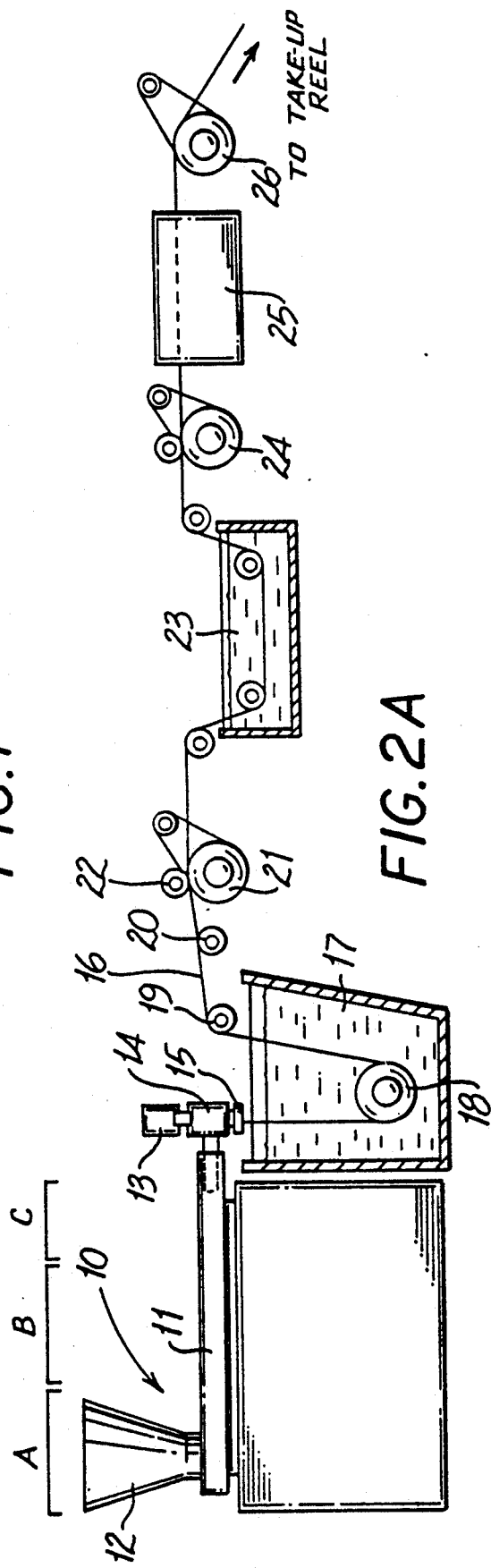
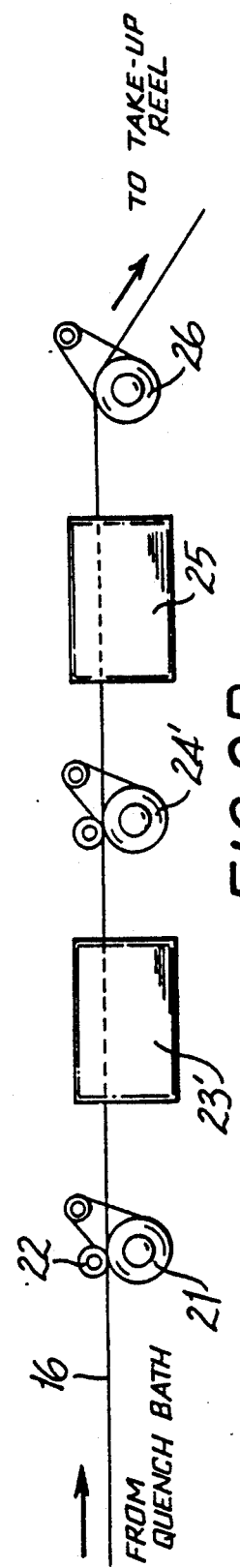
FIG. 1
FIG. 2A
FIG. 2B

ABSORBABLE POLYMERS AND SURGICAL ARTICLES MADE THEREFROM

FIELD OF THE INVENTION

The present invention relates to absorbable block copolymers having a block which is predominantly glycolide and a block which has glycolide, lactide and trimethylene carbonate linkages. This invention also relates to surgical articles made from such copolymers.

BACKGROUND OF THE INVENTION

Polymers and copolymers of, and surgical devices made from, lactide and/or glycolide and/or related compounds are well-known. See, e.g., U.S. Pat. Nos. 2,668,162, 2,683,136, 2,703,316, 2,758,987, 3,225,766, 3,268,486, 3,268,487, 3,297,033, 3,422,181, 3,442,871, 3,463,158, 3,468,853, 3,531,561, 3,565,869, 3,597,449, 3,620,218, 3,626,948, 3,636,956, 3,736,646, 3,739,773, 3,772,420, 3,733,919, 3,781,349, 3,784,585, 3,792,010, 3,797,499, 3,839,297, 3,846,382, 3,867,190, 3,987,937, 3,878,284, 3,896,802, 3,902,497, 3,937,223, 3,982,543, 4,033,938, 4,045,418, 4,057,537, 4,060,089, 4,137,921, 4,157,437, 4,243,775, 4,246,904, 4,273,920, 4,275,813, 4,279,249, 4,300,565, and 4,744,365, U.K. Pat. or Appln. Nos. 779,291, 1,332,505, 1,414,600 and 2,102,827, D. K. Gilding et al., "Biodegradable polymers for use in surgery-polyglycolic/poly (lactic acid) homo-and copolymers: 1, "*Polymer*, Volume 20, pages 1459-1464 (1979), and D. F. Williams (ed.), *Biocompatibility of Clinical Implant Materials*, Volume II, chapter 9: "Biodegradable Polymers" (1981).

Surgical devices prepared from copolymers containing lactide or glycolide and trimethylene carbonate have been described, for example, in U.S. Pat. No. 4,429,080 which describes glycolide-trimethylene carbonate random copolymers and triblock copolymers having glycolide end blocks and glycolide-trimethylene carbonate random copolymer middle blocks. The block copolymers described in the '080 patent contain no lactide.

As another example, U.S. Pat. No. 5,066,772 describes random copolymers of lactide and trimethylene carbonate and triblock copolymers having lactide end blocks and lactide-trimethylene carbonate random copolymer center blocks. The block copolymers of the '772 patent do not include a block which is predominantly glycolide. In addition, see U.S. Pat. Nos. 4,243,775; 4,300,565; 4,705,820; 4,891,263; 4,916,193; and 4,920,203.

SUMMARY OF THE INVENTION

It has now been found that absorbable surgical articles may be formed from a block copolymer comprising a first block formed from a polymer having glycolide as the predominant component thereof and a second block having glycolide, lactide and trimethylene carbonate linkages. A "predominant component" is a component which is present in an amount greater than fifty mole percent.

In particularly useful embodiments, the absorbable block copolymers of the present invention can be spun into fibers. These fibers are useful as monofilament sutures, can be braided to form multifilament sutures, or can be incorporated into absorbable or partially absorbable surgical elements.

The preferred copolymers of this invention have desirable physical characteristics such as shorter absorption times compared to glycolide/lactide copolymers while maintaining other physical characteristics comparable to the glycolide/glycolide-co-trimethylene carbonate/glycolide triblock copolymer of the prior art.

BRIEF DESCRIPTION OF THE DRAWINGS

FIG. 1 is a depiction of a needled suture in accordance with the present invention;

FIGS. 2A and 2B are a schematic illustration of an extrusion and stretching operation useful in producing sutures in accordance with this invention.

DETAILED DESCRIPTION OF THE INVENTION

Figure 3:
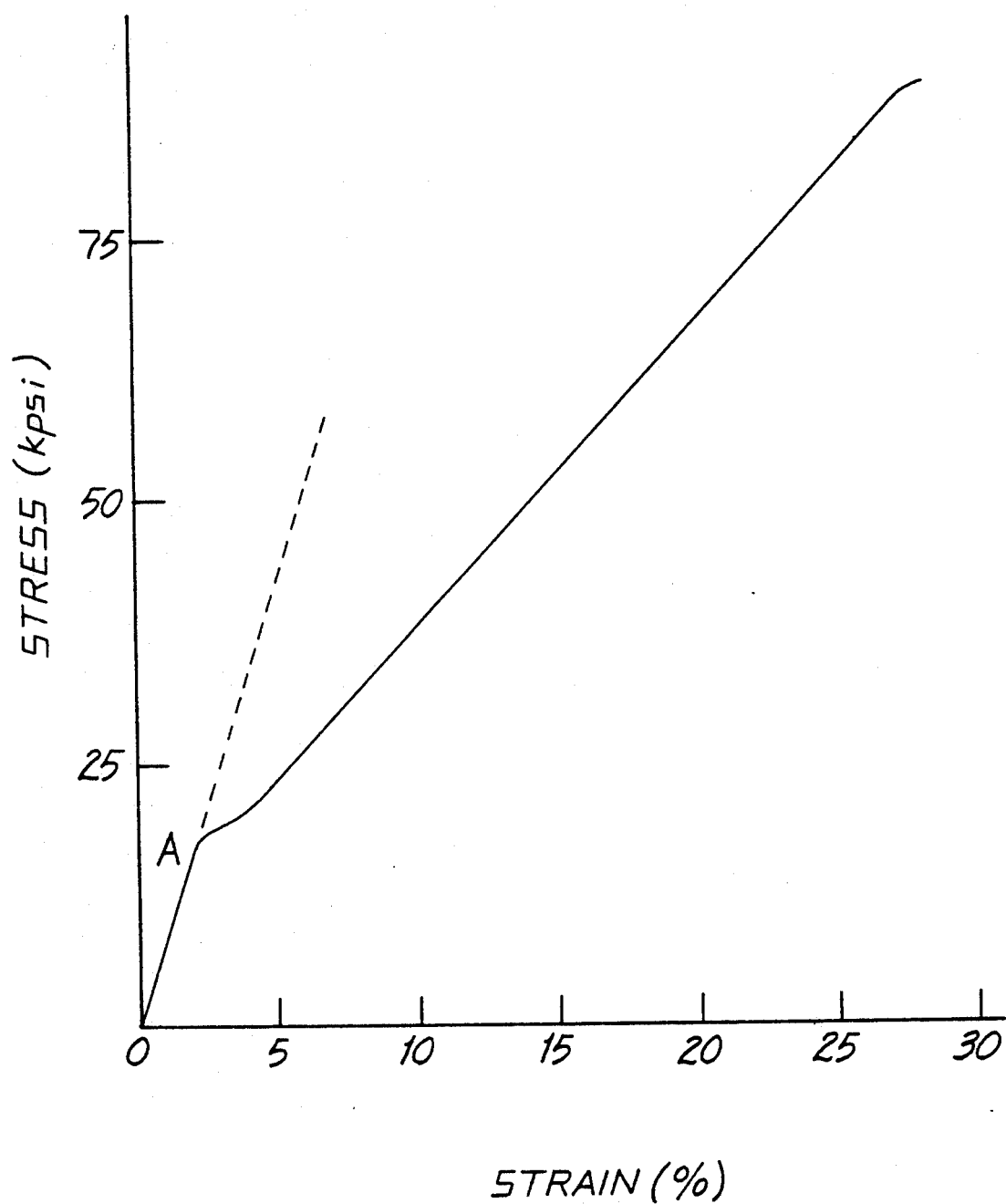
FIG. 3 illustrates the stress-strain behavior of a monofilament fiber prepared in accordance with the present invention.

In accordance with the present invention, it has been found that a block copolymer having two specific types of blocks, one having glycolide as the predominant component thereof and one having glycolide, lactide and trimethylene carbonate linkages, can advantageously be combined to form a block copolymer useful in forming surgical elements.

The block copolymer compositions of the present invention include a first block formed from a copolymer which has glycolide as the predominant component thereof. That is, glycolide comprises at least 50 mole percent of the first block. Preferably, glycolide comprises at least about 80 mole percent of the first block. Most preferably, the first block is a glycolide homopolymer. The glycolide may be copolymerized with any monomer which provides an absorbable copolymer to form the first block. Such monomers include but are not limited to lactide, p-dioxanone and ε-caprolactone. The copolymers of glycolide which form the first block can be random or block copolymers and can be synthesized by known methods. See, for example, U.S. Pat. Nos. 4,653,497; 4,838,267; 4,429,080; 4,605,730; and 4,788,979 the disclosures of which are incorporated herein by reference.

The second block of the compositions of this invention has glycolide, lactide and trimethylene carbonate linkages. Preferably, lactide is the predominant component of the second block. That is, lactide preferably comprises at least 50 mole percent of the second block. Most preferably, lactide comprises at least about 70 mole percent of the second block. In a particularly useful embodiment, the second block comprises about 80 mole percent of lactide the remainder of the block comprising equal proportions of glycolide and trimethylene carbonate. For purposes of the present invention, glycolide, lactide and trimethylene carbonate terpolymers having an inherent viscosity of from about 0.7 to about 1.5 dl/g measured at 30° C. and a concentration of 0.25 g/dl in chloroform or HFIP may generally be used as the second block.

The block copolymers of this invention may be prepared by preparing the individual polymers which make up the blocks and then copolymerizing these polymers to form a block or graft copolymer. Alternatively, a polymer having glycolide, lactide and trimethylene carbonate linkages may be prepared in a reactor and then the monomers needed to form the other block added directly to the reactor to thereby form the block copolymer.

In forming the block copolymers of this invention, the first, predominantly glycolide block may be present in an amount from about 10 to about 90 percent by weight based on the weight of the final block copolymer. The second, terpolymer block may be present in an amount from about 10 to about 90 weight percent based on the weight of the final block copolymer. Preferably, the second block comprises between about 10 and about 25 weight percent of the block copolymer. In a particularly useful embodiment, the first block comprises about 85 weight percent and the second block comprises about 15 weight percent of the final block copolymer. The copolymers of the present invention have a molecular weight such that their inherent viscosity is from about 0.8 to about 2 dl/g preferably from about 1.3 to about 1.7 dl/g measured at 30° C. at a concentration of 0.25 g/dl in chloroform or hexafluoroisopranol (HFIP).

The block copolymers of this invention can be formed into surgical articles using any known technique, such as, for example, extrusion, molding and/or solvent casting. The copolymers can be used alone, blended with other absorbable compositions, or in combination with non-absorbable components. Fibers made from the copolymers of this invention can be knitted or woven with other fibers, either absorbable or nonabsorbable, to form meshes or fabrics. The compositions of this invention can also be used as an absorbable coating for surgical devices. Preferably, however, the copolymers are spun into fibers to be used as sutures, either monofilament or multifilament. The spinning and braiding of copolymer fibers to form multifilament sutures can be accomplished by any known technique such as those described, for example, in U.S. Pat. Nos. 5,019,093 and 5,059,213, the disclosures of which are incorporated herein by reference.

A wide variety of surgical articles can be manufactured from the copolymers of the present invention. These include but are not limited to sutures, staples, clips and other fasteners, wound dressings, drug delivery devices, pins, screws and other implants.

Surgical articles made from the polymers of this invention can be used to secure tissue in a desired position. A suture in accordance with the present invention, suture 101, may be attached to a surgical needle 100 as shown in FIG. 1 by methods well known in the art. Wounds may be sutured by approximating tissue and passing the needled suture through tissue to create would closure. The needle preferably is then removed from the suture and the suture tied.

As previously mentioned, the surgical elements of the present invention exhibit shorter absorption times compared to glycolide/lactide copolymers and other physical characteristics comparable to the glycolide-glycolide/trimethylene carbonate-glycolide ABA triblock copolymers of the prior art.

The following examples are illustrative of the copolymers of the present invention and surgical elements made therefrom.

EXAMPLE 1

Glycolide (63.45 grams), lactide (630.75 grams) and trimethylene carbonate (55.79 grams) are added to a reactor along with 5 grams of diethylene glycol and 0.74 grams of stannous octoate. The contents of the reactor are dried at 24°±2° C. for 16 hours. The mixture is heated at 180° C. for 3 hours in a nitrogen atmosphere. After 3 hours stirring is begun and these conditions are maintained for 24 hours. The glycolide/lactide/trimethylene carbonate is then sampled.

The setting for the temperature of the reactor is then increased to 230° C. When the temperature of the reactor reaches 185° C., 500 grams of glycolide are added with continued stirring. When the temperature in the reactor reaches 210°–220° C., 3750 grams of glycolide are added with continued stirring. The polymerization is continued at 230° C. for about one hour.

The reaction product is isolated, comminuted and treated to remove residual reactants using known techniques. The copolymer is then heated under vacuum to remove water, residual solvent, and/or unreacted monomer.

FIGS. 2A and 2B schematically illustrate preferred extrusion and stretching operations for producing monofilaments of the copolymers of this invention. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of the block copolymer are introduced to the extruder through drier-hopper 12.

Motor-driven metering pump 13 delivers extruded copolymer at a constant rate to spin pack 14 and thereafter through spinneret 15 possessing one or more orifices of desired diameter to provide a molten monofilament 16 which then enters quench bath 17, e.g., containing water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling of the monofilament in some unpredictable manner. In general, barrel zone A of the extruder can be maintained at a temperature of from about 160° to 220° C., zone B at from about 180° to 230° C. and zone C at from about 190° to about 240° C. Additional temperature parameters include: metering pump block 13 at from about 180° to about 230° C., spin pack 14 at from about 180° to about 230° C., spinneret 15 at from about 190° to about 240° C. and quench bath 17 at from about 20° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sizes 4/0 to 8/0, monofilament 16 is drawn through heating unit 23, which can be an oven chamber or a hot liquid (such as water and glycerol) trough, by means of second godet 24 which rotates at a higher speed than first godet 21 thereby stretching the monofilament from three to nine times its original length. Where heating unit 23 is an oven chamber, its temperature is advantageously maintained at from about 40° to about 140° C. and preferably from about 50° to about 120° C. In the case of larger sutures, e.g., sizes 2 to 3/0, it is preferred that heating unit 23 be a hot liquid trough or bath which is maintained at a temperature of from about 30° to about 98° C. and preferably from about 40° to about 90° C.

After the above mentioned operation it is preferred to pass the monofilament through a second heating unit, e.g., maintained at a temperature of from about 40° to about 140° C. and preferably from about 50° to about 120° C., by means of a third godet to heat-treat the monofilament prior to the equilibration and annealing operations. This second heat treatment results in on-line relaxation, or shrinkage, of the monofilament, e.g., for a recovery of from about 85 to about 97 percent, and preferably from about 90 to about 95 percent, of the stretched length of the monofilament. In order to accommodate this on-line shrinkage in the monofilament, the third godet is driven at a speed which is somewhat less than that of the second godet.

Following stretching and orientation (and, optionally, the aforedescribed second heat treating step), monofilament 16 from godet 24 is taken up on a spool which is then set aside for a period of time sufficient to permit the monofilament to achieve a condition of equilibration as previously defined. While the period of equilibration may vary depending on the particular copolymer composition employed and/or the conditions under which the copolymer is extruded, cooled and oriented, in most cases storage of the monofilament following its orientation for at least about 3 days, preferably at least about 24 hours and more preferably at least about 2 hours. It is generally preferred that the spooled monofilament be stored at ambient temperature, e.g., 18°-23° C., and a dew point below −12° C.

Thereafter, annealing may be accomplished by shrinkage of the suture, e.g., for a recovery of from about 75 to about 95 percent, and preferably from about 80 to about 90 percent, of its stretched length.

In carrying out the annealing operation, the desired length of equilibrated suture may be wound around a creel and the creel placed in a heating cabinet circulated with nitrogen and maintained at the desired temperature, e.g., 70° C. After a suitable period of residency in the heating cabinet, e.g., about 20 minutes to 24 hours, the suture will have undergone shrinkage, e.g., to about 85% of the stretched length for sutures of sizes 2 to 3/0, to about 90% of the stretched length for sutures of sizes 4/0 and 5/0 and essentially no shrinkage in the case of sutures of sizes 6/0 to 8/0. The creel may be rotated within the heating cabinet in order to insure uniform heating of the monofilament or the cabinet may be of the circulating hot air type in which case uniform heating of the monofilament will be achieved without the need to rotated the creel. Thereafter, the creel with its annealed suture is removed from the heating cabinet and when returned to room temperature, the suture is removed from the creel, conveniently by cutting the wound monofilament at opposite ends of the creel.

The sutures, optionally attached to surgical needles, are then ready to be packaged and sterilized.

EXAMPLE 2

Monofilament sutures manufactured in accordance with the abovedescribed process using the copolymer of Example 1 were tested for straight pull strength, Young's modulus and in vitro strength retention. Straight pull strength was tested in accordance with the test procedure described in ASTM D-2256. An Instron Tensile Tester Model No. 1122 (Instron Corporation, Canton, Mass.) was used to determine straight-pull strength. Knot pull tensile strength was tested in accordance with U.S.P. XXI, tensile strength sutures (881). Young's modulus, which is a measurement of flexibility, is the initial modulus as determined from the slope of stress-strain curves produced in the straight-pull strength tests. Young's modulus is the ratio of applied stress to strain in the elastic region (initial linear portion of curves, AO) as illustrated in FIG. 3. The stress-strain curve of FIG. 3 represents the average of five tests on lengths of the same fibrous material. The in vitro strength retention of the suture was tested as follows:

To simulate in vivo conditions, the suture samples were stored in a container filled with Sorenson's buffer solution at 37° C. After various period of time, the suture samples were then removed from the container to test their knot-pull strength, using a Instron tensile tester. In vitro knot-pull strength retention is indicative of in vivo strength retention.

The results of the tests are presented in Table I. In the strength retention data reported in Table I, $T_n$ represents the time elapsed in weeks since the sample was placed in the solution, with n representing the number of weeks. For comparison purposes, the same tests were conducted on a Maxon suture, which is made from a glycolide/glycolide-trimethylene carbonate/glycolide copolymer (commercially available from Davis & Geck, Danbury, CT).

TABLE I

| Suture | Straight Pull Strength (kpsi) | Knot Pull Strength (kpsi) | Young's Modulus (Kpsi) | In Vitro Strength Retention (% Strength Remaining) | | | | |
|---|---|---|---|---|---|---|---|---|
| | | | | $T_1$ | $T_2$ | $T_3$ | $T_4$ | $T_6$ |
| Example 2 | 100 | 66 | 1480 | 65 | 61 | 0 | — | — |
| MAXON | 78–88 | 41–70 | 435–495 | — | 66 | — | 17 | 0 |

As the data in Table I demonstrates, the suture made of a copolymer of the present invention showed less in vitro strength retention while demonstrating acceptable straight and knot pull strengths and Young's modulus.

What is claimed is:

1. A block copolymer comprising:
   a) a first block formed from a polymer having glycolide as the predominant component thereof; and
   b) a second block having glycolide, lactide and trimethylene carbonate linkages.

2. A copolymer as in claim 1 wherein said first block comprises glycolide in an amount greater than about 70 mole percent.

3. A copolymer as in claim 1 wherein said first block comprises a homopolymer of glycolide.

4. A copolymer as in claim 1 wherein said second block comprises lactide as the predominant component.

5. A copolymer as in claim 1 wherein said second block comprises about 80 percent lactide.

6. A copolymer as in claim 1 wherein said first block comprises from about 10 to about 90 percent by weight of the block copolymer.

7. A copolymer as in claim 1 wherein said second block comprises from about 10 to about 90 percent by weight of the copolymer.

8. A copolymer as in claim 1 wherein said first block comprises about 85 percent by weight of the block copolymer and said second block comprises about 15 percent by weight of the block copolymer.

9. A surgical article comprising one or more fibers made from a block copolymer having a first block comprising a polymer having glycolide as the predominant component thereof and a second block having glycolide, lactide and trimethylene carbonate linkages.

10. A surgical article as in claim 9 wherein said first block comprises glycolide in an amount greater than about 70 mole percent.

11. A surgical article as in claim 9 wherein said first block comprises a homopolymer of glycolide.

12. A surgical article as in claim 9 wherein said second block comprises lactide as the predominant component.

13. A surgical article as in claim 9 wherein said second block comprises about 80 percent lactide.

14. A surgical article as in claim 9 wherein said first block comprises from about 10 to about 90 percent by weight of the block copolymer.

15. A surgical article as in claim 9 wherein said second block comprises from about 10 to about 90 percent by weight of the copolymer.

16. A surgical article as in claim 9 wherein said first block comprises about 85 percent by weight of the block copolymer and said second block comprises about 15 percent by weight of the block copolymer.

17. A surgical article as in claim 9 wherein said surgical element is a suture.

18. An absorbable surgical suture comprising a block copolymer having a first block formed from a polymer having glycolide as the predominant component thereof and a second block having glycolide, lactide and trimethylene carbonate linkages.

19. An absorbable suture as in claim 18 wherein said suture is a monofilament suture.

20. A method of closing a wound comprising suturing with a suture made at least in part from the copolymer of claim 1.

* * * * *